Aug. 26, 1947. W. B. CLARKE Plant Pat. 754
LILAC PLANT
Filed Aug. 7, 1946
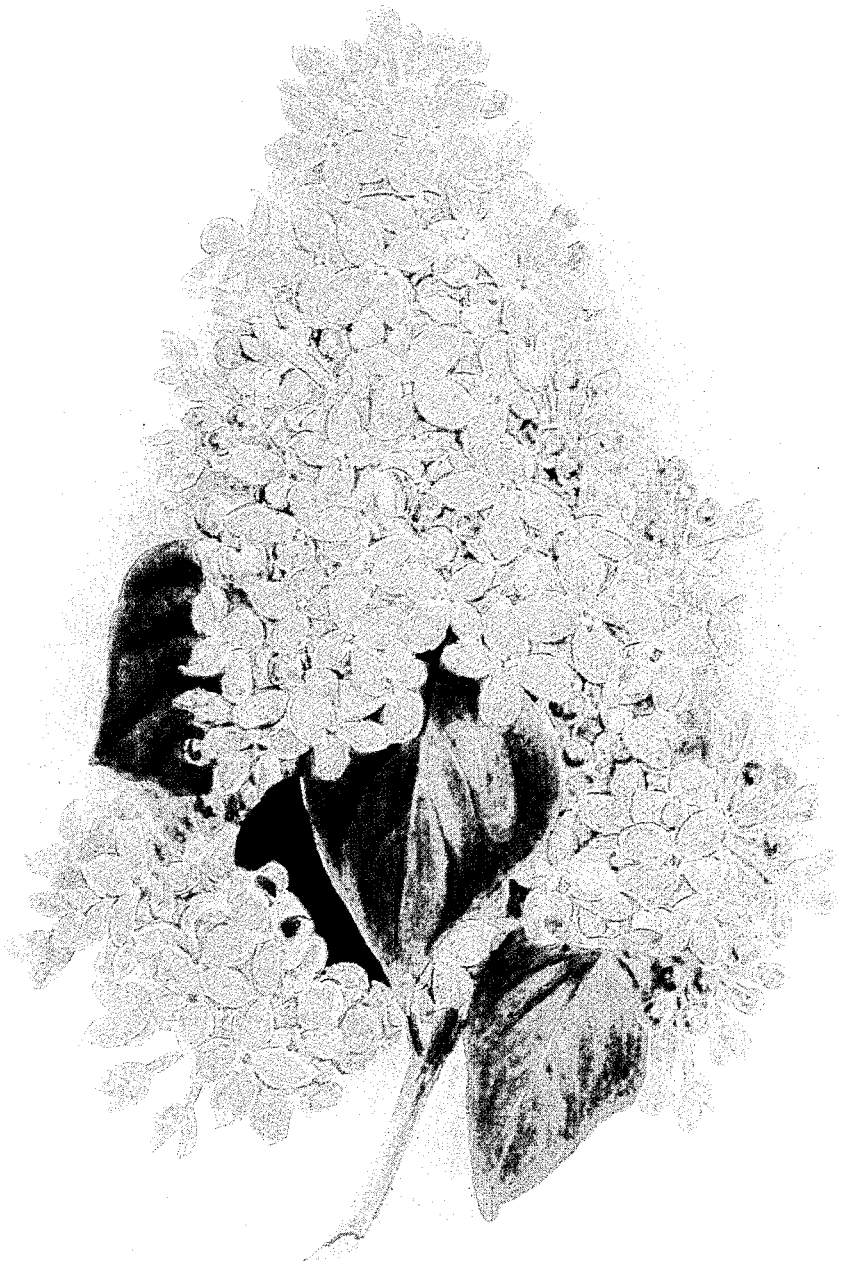
WITNESS
Addison J. Avery
INVENTOR
WALTER BOSWORTH CLARKE,
Rummler, Rummler & Davis,
ATTY'S.

Patented Aug. 26, 1947

Plant Pat. 754

UNITED STATES PATENT OFFICE

754

LILAC PLANT

Walter Bosworth Clarke, San Jose, Calif., assignor to W. B. Clarke & Co., San Jose, Calif., a partnership Application August 7, 1946, Serial No. 689,037

1 Claim. (Cl. 47—60)

The present discovery relates to a new and distinct variety of *Syringa vulgaris*, resulting from a cross made by me between a seedling of an unnamed double variety as the seed parent and another unnamed seedling as the pollen parent.

Its novelty resides primarily in the unique coloring of the flowers at the different stages of their development, and in the enormous size of the individual florets, the great size and shape of the thyrses, the large green leaves and the vigorous, erect growth of the bush. The plant is the result of definite breeding efforts carried on by me and my associates since 1932. Asexual reproduction by budding and grafting has proved these features to be firmly fixed.

In general plant structure this new variety is similar to the well-known *Syringa vulgaris*. But this new variety differs distinctly from all varieties of *Syringa vulgaris* known to me. The individual flower has the usual bell-shaped, four-toothed calyx, and salverform, four-lobed corolla. The leaves are a deep green in color and very large but are otherwise similar in form and texture to the parent strain, being ovate-cordate in form and growing opposite each other in pairs. It is a vigorous grower. There are no large plants of this new variety in existence at this time, but its buds and grafts made for testing have both bloomed when only a year old.

The accompanying painting shows a panicle of the new lilac in its natural colors.

Referring to the novel characteristics of this new variety; each floret is enormous in size, up to one and one-half inches wide, thus giving great size to the thyrses which, instead of being conical in shape as are those of most lilacs, show a pronounced flattening on four sides, giving the effect of an elongated four-sided pyramid. The flower is particularly striking in the half-open stage when the unopen buds toward the top of the cluster are soft pinkish mauve in color while the fully developed flowers at the bottom have a beautiful sky-blue tone.

The following is an itemized description in schedule form of the new variety:

Parentage: Seedling.
*Seed parent.*—An unnamed double variety.
*Pollen parent.*—Unnamed.
Class: *Syringa vulgaris* variety.

*Flower*

Floret:
*Size.*—Enormous; up to 1½ inches wide.
*Form.*—Four-lobed, salverform corolla.
*Color.*—Mauve in bud, opening sky-blue.
Panicles:
*Size.*—Massive with large clusters of very large florets.
*Form.*—Pyramidal (4-sided).
*Borne.*—Usually singly, or paired.
*Lasting quality.*—On plant: usual length of time; as a cut flower: particularly good.

*Plant*

Form: Tree or bush; growth is erect and usually vigorous.
Height: Maximum unknown as yet.
Foliage: Quantity—ample.
Size of leaf: One of the largest known in lilacs.
Texture: Usual.
Shape: Broadly ovate-cordate; acuminate.

The color designations according to "A Dictionary of Color by Maerz and Paul" are as follows:

| Section | Color | Plate | Ltr. | No. |
|---|---|---|---|---|
| Flower: | | | | |
| General tone of body shading into | Blue | 41 | E | 3 |
| Face of open florets | do | 33 | A | 6 |
| Shading into open florets | do | 33 | A | 7 |
| Back of floret | | 41 | J | 4 |
| Buds | | 43 | L | 6 |
| Center eye | | 9 | K | 6 |
| Leaf | | 21 | L | 8 |

The hereindescribed plant is particularly characterized by the large, crowded panicles which increase and concentrate the mass of attractive color; the unique and unusual coloring at its different stages of development; the enormous size of the individual floret and of the dark green leaves; its fragrance and its particularly good lasting qualities as a cut flower.

Having thus disclosed my invention, I claim:

A new and distinct variety of *Syringa vulgaris* plant, substantially as described, being characterized by the progressively changing and distinctive colors appearing during its different stages of development; by the enormous size both of the individual floret and the panicle; by its large green leaves and superior keeping qualities.

WALTER BOSWORTH CLARKE.